(12) United States Patent
Cotéet al.

(10) Patent No.: US 6,885,882 B2
(45) Date of Patent: Apr. 26, 2005

(54) METHOD AND APPARATUS FOR NON-INVASIVE GLUCOSE SENSING THROUGH THE EYE

(76) Inventors: Gerard L. Coté, 1204 Neal Pickett Dr., College Station, TX (US) 77840; Justin S. Baba, Wellborn Heights, Unit 9, 16567 FM2154 Rd., College Station, TX (US) 77845

( * ) Notice: Subject to any disclaimer, the term of this patent is extended or adjusted under 35 U.S.C. 154(b) by 163 days.

(21) Appl. No.: 10/445,648

(22) Filed: May 27, 2003

(65) Prior Publication Data

US 2003/0225321 A1 Dec. 4, 2003

Related U.S. Application Data

(60) Provisional application No. 60/383,737, filed on May 28, 2002.

(51) Int. Cl.⁷ .................................................. A61B 5/00
(52) U.S. Cl. ..................................................... 600/319
(58) Field of Search ................................ 600/310, 316, 600/318, 319; 356/364, 368, 369

(56) References Cited

U.S. PATENT DOCUMENTS

| | | | | |
|---|---|---|---|---|
| 5,209,231 A | * | 5/1993 | Cote et al. ................... | 600/316 |
| 5,398,681 A | * | 3/1995 | Kupershmidt ................ | 600/316 |
| 5,448,992 A | * | 9/1995 | Kupershmidt ................ | 600/316 |
| 5,457,535 A | * | 10/1995 | Schmidtke et al. .......... | 600/310 |
| 5,671,301 A | * | 9/1997 | Kupershmidt ................... | 385/1 |
| 5,788,632 A | * | 8/1998 | Pezzaniti et al. ............ | 600/316 |
| 6,166,807 A | * | 12/2000 | Kawamura et al. .......... | 600/316 |
| 6,188,477 B1 | * | 2/2001 | Pu et al. ..................... | 356/491 |
| 6,246,893 B1 | * | 6/2001 | Gobeli ........................ | 600/318 |
| 6,370,407 B1 | * | 4/2002 | Kroeger et al. .............. | 600/319 |

* cited by examiner

*Primary Examiner*—Eric F. Winakur
(74) *Attorney, Agent, or Firm*—Neil A. Steinberg

(57) ABSTRACT

There are many inventions described and illustrated herein. In one aspect, the present invention is a system and technique for non-invasively measuring, monitoring, inspecting, characterizing, determining and/or evaluating the blood glucose level in the aqueous humor of the eye of a patient (for example, a diabetic). In one embodiment, the present invention employs a plurality of wavelengths of light (for example, more than three) to measure, monitor, characterize, determine and/or evaluate the blood glucose level or concentration of a patient. The plurality of wavelengths of light may be directed into the aqueous humor of the eye and the reflected light (i.e., the light reflected by the eye) is detected and analyzed to provide information which is representative of the blood glucose level or concentration of the patient.

20 Claims, 11 Drawing Sheets

METHOD AND APPARATUS FOR NON-INVASIVE GLUCOSE SENSING THROUGH THE EYE

CROSS-REFERENCE TO RELATED APPLICATIONS

This application claims priority to U.S. Provisional Application Ser. No. 60/383,737, entitled "Method and Apparatus for Noninvasive Glucose Sensing Through the Eye", filed May 28, 2002. The contents of this provisional application are incorporated by reference herein in their entirety.

BACKGROUND OF THE INVENTION

This invention relates to techniques, systems and devices that are used to characterize, measure, monitor and/or evaluate the blood glucose level of a patient, for example, a human. More particularly, in one aspect, the present invention measures, monitors and/or evaluates, in a non-invasive manner, the glucose concentration in the aqueous humor of the eye as a way of monitoring blood glucose levels of a patient.

More than ten million people in the United States of America suffer from diabetic hyperglycemia (an increased level of glucose in the blood) and hypoglycemia (a reduced level of glucose in the blood). Individuals afflicted with either disease in a severe form typically perform an invasive blood glucose level analysis four or more times a day. Typically, such an analysis requires the patient to do a finger or forearm stick to remove blood. Thereafter, the blood is placed on an electrochemical sensor or enzymatic-based colorimetric strip to determine the glucose level.

A significant disadvantage of this conventional technique is that it is "invasive"—in that the technique often entails extraction of a small amount of blood from the patient's finger or a forearm stick. This invasive technique is painful, embarrassing, opens the body to infection, and may ultimately result in less frequent monitoring which, in turn, results in poor or insufficient glucose monitoring and control.

Recently a device known as a "GlucoWatch" has been introduced to the market that is based on a principle of reverse iontophoresis. Reverse iontophoresis senses glucose containing fluid through the skin of the patient. The Gluco-Watch typically requires a reading be taken every 20 minutes to obtain glucose "trending" information, which may be employed to monitor the patient's blood glucose level.

Several polarmetric optical approaches to non-invasive glucose detection have been proposed (See, for example, U.S. Pat. Nos. 5,209,231; 5,398,681; 5,448,992; 5,457,535; 5,448,992; 5,671,301; 5,788,632; 6,188,477; 6,370,407; and 6,246,893). While these systems and techniques are non-invasive, and as such, do not include the "pain" that accompanies an "invasive" system and technique, these non-invasive systems and techniques have numerous shortcomings including, for example, problems or shortcoming with addressing the "adverse" impact of eye motion or artifact, corneal birefringence, and/or limited sensitivity and specificity of blood glucose level measurement and monitoring accuracy.

There is a need for a non-invasive (or minimally invasive) system, device and technique that overcomes one, some or all of shortcomings of the conventional techniques. For example there is a need for a non-invasive (or minimally invasive) system, device and technique that relatively accurately measures, monitors, characterizes and/or evaluates the blood glucose level of a patient. Moreover, there is a need for an improved optically based system, device and technique that measures, monitors, characterizes and/or evaluates the blood glucose level of a patient that overcomes, addresses or minimizes the "adverse" impact of eye motion or artifact and/or corneal birefringence.

SUMMARY OF THE INVENTION

There are many inventions described and illustrated herein. In a first principal aspect, the present invention is an apparatus and a technique to noninvasively measure glucose concentrations in the aqueous humor of the eye to thereby monitor or characterize blood glucose levels of a patient. The apparatus and technique of this aspect of the present invention includes an optical technology based on multi-wavelength, multi-detector, optical polarimetry and a mechanism to couple the light into the aqueous humor of the eye.

In another principal aspect, the present invention is a system for sensing an analyte in the aqueous humor of the eye of a patient using a light source (for example, a plurality of lasers) unit that provides at least three light beams wherein each light beam includes a wavelength and modulation frequency that is different from the other light beams. The system of this aspect of the invention further includes a polarization mechanism, optically positioned to receive the light beams, and to linearly polarize each light beam. A detector unit receives the light beams reflected by the eye and detects a change in polarization of the light beams, wherein the polarization of the light beams are changed as a result of contact with analyte in the aqueous humor of the eye. A processing unit, coupled to the detector unit determines the concentration of analyte in the aqueous humor of the eye using information which is representative of the change in polarization of the light beams.

In one embodiment of this aspect of the present invention, the polarization mechanism may linearly polarize each light beam at any angle. In one embodiment, the polarization mechanism is a polarization rotator, for example, a faraday rotator. Indeed, the polarization rotator may feed back an output voltage proportional to the fundamental harmonic of the light beam and/or may modulate the polarization vector of at least two of the light beams.

In another embodiment of this aspect of the present invention, the system may also include a beam steering mechanism (for example, an electro-optic device such as a piezo-electric mirror) to direct the beams through the anterior chamber of the eye of the patient.

In yet another principal aspect, the present invention is a system for sensing an analyte in the aqueous humor of the eye of a patient using a light source (for example, a plurality of lasers) unit that provides at least three light beams wherein each light beam includes a wavelength and modulation frequency that is different from the other light beams. The system of this aspect of the invention further includes a polarization mechanism, optically positioned to receive the light beams, and to linearly polarize each light beam.

In addition, the system may include a beam steering mechanism (for example, an electro-optic device such as a piezo-electric mirror), optically positioned to receive linearly polarized light beams, in order to direct the linearly polarized light beams through the anterior chamber of the eye of the patient. An image tracking system, coupled to the beam steering mechanism, may be employed to control the beam steering mechanism in response to motion of the eye of the patient.

A detector unit receives the light beams reflected by the eye and detects a change in polarization of the light beams, wherein the polarization of the light beams are changed as a result of contact with analyte in the aqueous humor of the eye. A processing unit, coupled to the detector unit determines the concentration of analyte in the aqueous humor of the eye using information which is representative of the change in polarization of the light beams.

In one embodiment of this aspect of the present invention, the polarization mechanism (for example, a polarization rotator such as a faraday rotator) may linearly polarize each light beam at any angle. The polarization rotator may also modulate the polarization vector of at least two of the light beams.

BRIEF DESCRIPTION OF THE DRAWINGS

In the course of the detailed description to follow, reference will be made to the attached drawings. These drawings show different aspects of the present invention and, where appropriate, reference numerals illustrating like structures, components, materials and/or elements in different figures are labeled similarly. It is understood that various combinations of the structures, components, materials and/or elements, other than those specifically shown, are contemplated and are within the scope of the present invention.

FIG. 8 reveals that the presence of motion artifact may be due in large part to respiration and, to a lesser degree, the cardiac cycle in our detected signal;

DESCRIPTION OF DETAILED EMBODIMENTS

There are many inventions described and illustrated herein. In one aspect, the present invention is directed to a technique of, and system and device for measuring, monitoring, inspecting, characterizing, determining and/or evaluating the blood glucose level of a patient using a non-invasive (or minimally invasive) approach. In one embodiment, the present invention employs a plurality of wavelengths of light (for example, more than three) to measure, monitor, characterize, determine and/or evaluate the blood glucose level or concentration of a patient. The plurality of wavelengths of light may be directed into the aqueous humor of the eye. Thereafter, the light is detected and analyzed to provide information which is representative of the blood glucose level or concentration of a patient.

In those instances where a plurality of detectors are employed, the light reflected by the aqueous humor of the eye may be separated according to predetermined wavelengths (for example, using wavelength filters) and measured or sampled by one of the detectors. In this way, a "dedicated" detector may synchronously demodulate a predetermined wavelength of the reflected light and thereby sense, measure, determine, monitor and analyze the rotation of polarized light in the aqueous humor of the eye.

In one embodiment, each wavelength may have multiple polarization angles and/or multiple frequencies. In this way, the detector may more easily discriminate between the different wavelengths of light as well as synchronously demodulate each wavelength of the reflected light using the detector.

In another principal aspect, the system of the present invention may also include an image tracking system that tracks the motion of the eye and controls a beam steering device in order to maintain appropriate, desired and/or correct alignment of beams relative to or in the presence of eye motion or movement. In one embodiment, the image tracking system controls an electro-optic device (for example, a piezo-electric mirror). Indeed, in one embodiment, a second electro-optic device works in combination with the image tracking system to maintain appropriate, desired and/or correct alignment of the beam that exits the eye in order to accommodate eye motion or movement relative to the detection and analyzing optics/electronics.

In short, the image tracking system tracks eye motion to maintain the light beam in the proper, suitable and/or desired orientation through the anterior chamber of the eye in the presence of eye motion, which may include reflection of the light beam off of the iris or lens of the eye. Moreover, the present invention may also include a visible stimulus (for example, an LCD or CRT display) to encourage the patient to maintain the eye focused and steady during operation of system. A visible stimulus may more easily permit the patient to fixate the eye and thereby remove gross motion artifacts.

Figure 1:
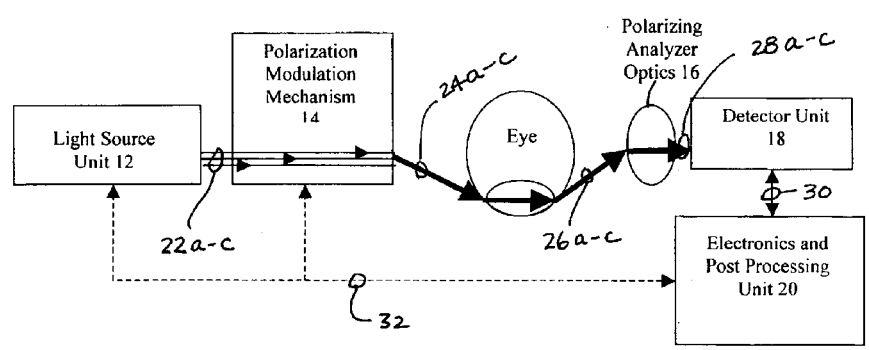
FIG. 1 is a block diagram representation of an embodiment according to one aspect of the present invention.

With reference to FIG. 1, in one embodiment, system 10 of the present invention includes light source unit 12, polarization modulation mechanism 14, polarizing analyzer optics 16, detector unit 18 and electronics and post processing unit 20. The light source unit 12 provides light having three or more wavelengths 22 (hereinafter for simplicity and/or illustrative purposes identified as 22a–22c; it is to be understood that more than three wavelengths 22 may be employed herein).

The light 22a, 22b and 22c is applied to polarization modulation mechanism 14 (for example, a faraday rotator and electro-optic polarization rotator, such as birefringent crystals and pockel cells) which, in one embodiment, rotates the polarization vectors of light 22a, 22b and 22c as a function of the wavelength. In another embodiment, polarization modulation mechanism 14 rotates light 22a, 22b and 22c in a predetermined and controlled manner, independent of the wavelength of light 22a, 22b and 22c. Regardless of the type or form of modulation, polarization modulation mechanism 14 outputs the modulated light 24a, 24b and 24c, which is associated with or corresponds to light 22a, 22b and 22c, respectively.

The light 24a, 24b, and 24c is directed to the aqueous humor of the eye and modified by, among other things the glucose analyte in the eye as well as birefringence caused by the optics of the eye. The modified light 26a, 26b and 26c is received by polarization analyzer optics 16. The polarization analyzer optics 16 (for example, a polarization beam splitter such as a Wollaston prism) provides a variable output of the polarization after modification by the glucose concentration in the aqueous humor of the eye. In this way, system 10 may discriminate between linear birefringence and rotation caused by the glucose analyte.

The output of polarization analyzer optics 16 (i.e., light 28a, 28b and 28c) is provided to detector unit 18 which measures the intensity of light 28a, 28b and 28c. In short, the intensity of light 28a, 28b and 28c is dependent on the polarization rotation due to the analytes including glucose, the birefringence of the eye, and the modulation of the polarization vector. The detector unit 18 converts that intensity into an electrical representative thereof, for example a current or voltage. The output of detector unit 18 is provided to electronics and post processing unit 20 via transmission elements 30a–c (for example, wires or optical couplers). In response, electronics and post processing unit 20 analyzes the data which is representative of the glucose concentration.

The electronics and post processing unit 20 may also be electrically coupled to light source unit 12 and polarization modulation mechanism 14. In this way, electronics and post processing unit 20 may control and/or monitor the operation of light source unit 12 and polarization modulation mechanism 14.

Figure 2A:
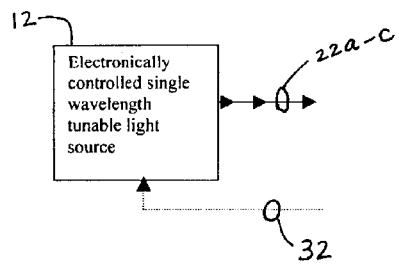
FIGS. 2A–2D illustrate embodiments for producing multiple wavelengths of light either sequentially in time with a single wavelength tunable source (FIG. 2A), sequentially in time with a multi-wavelength broadband source and optical wavelength tunable filter (FIG. 2B), spatially with a single multi-wavelength source and spatial filters (FIG. 2C), and with the use of multiple sources at various wavelengths (FIG. 2D)

In one embodiment, light source unit 12 may include one or more light sources to generate light 22a–c, each having a different wavelength. For example, with reference to FIG. 2A, in one embodiment, light source 12 is an electronically controlled, single tunable light source. In this embodiment, two or more wavelengths of light are produced from a single broadband source separated in a short time sequence (microseconds or less) using, for example, a tunable laser.

Figure 2B:
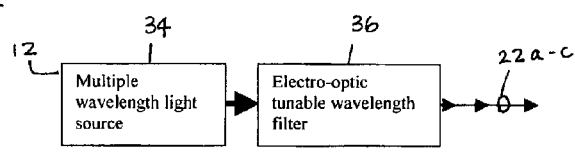

With reference to FIG. 2B, in another embodiment, light source 12 includes multiple wavelength light source 34 and electro-optic tunable wavelength filter 36 to generate and provide light 22a–c having different wavelengths. In this embodiment, two or more wavelengths of light are produced from a single broadband source separated in a short time sequence (for example, microseconds or less) using tunable wavelength filter 36.

Figure 2C:
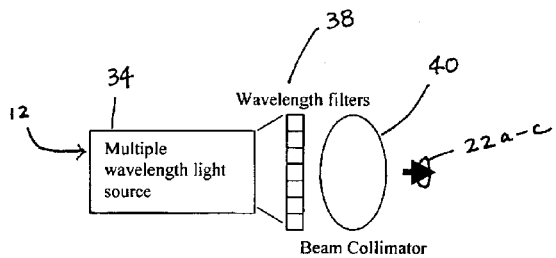

With reference to FIG. 2C, in another embodiment, light source 12 may include multiple wavelength single source 34 and wavelength filters 38 to generate and provide light 22a–c having different wavelengths. Thereafter, a beam collimator may direct the light having a plurality of wavelengths to polarization modulation 14. Thus, in this embodiment, two or more wavelengths are produced from a broadband source 34, in a spatial manner, using, for example, multi-wavelength spatial filter 38 and beam collimator 40. It should be noted that a plurality of beam splitters, wavelength filters, and beam combiners may also be employed to spatially generate light 22a–c, each having a different wavelength.

Figure 2D:
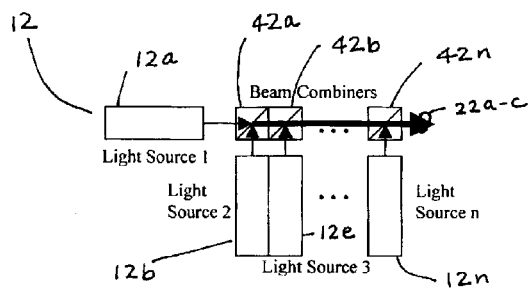

In addition, with reference to FIG. 2D, in another embodiment, a plurality of light sources 12a–n are arranged, in conjunction, with beam combiners 42a–n to generate and provide light 22a–c having different wavelengths. In this embodiment, two or more wavelengths are produced with two or more light sources, which for example may be laser light sources or LED light sources and which may be modulated at separate frequencies.

One set of embodiments of the present invention employ different input polarization states for each wavelength of light 22a–c, and the ac-polarization modulation of all the wavelengths, to thereby modulate the polarization of light 22a–c and reduce, eliminate or minimize the adverse impact of ambient optical noise due to, for example, room lights. In this way, system 10 may employ a synchronous detection technique, as described in detail below.

Figure 3A:
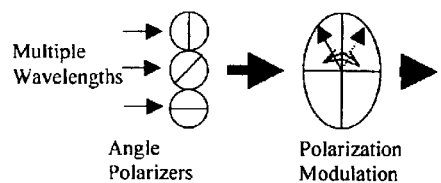
FIGS. 3A–3C illustrate embodiments of the polarization rotator according to various aspects of the present invention, including a mechanism to produce fixed polarization angles for each wavelength with one way of modulating the polarization vector for all wavelengths (FIG. 3A), a mechanism to produce multiple discrete polarization angles for each wavelength with a second way of modulating the polarization vector for all wavelengths (FIG. 3B), and a mechanism of producing fixed or multiple polarization angles for each wavelength when multiple sources are used to produce multiple wavelengths with a second way of modulating the polarization vector for all wavelengths (FIG. 3C)

With reference to FIG. 3A, in one embodiment, the input polarization may be set to a fixed, predetermined polarization angle—for example horizontal, vertical, or ±45 degrees for each wavelength. Alternatively, left or right circularly polarized light can be used.

Figure 3B:
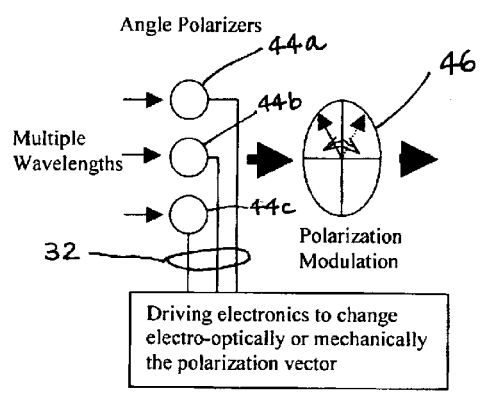

With reference to FIG. 3B, in another embodiment, angle polarizers 44a–c may be employed to set to a predetermined polarization angle for light 22a–c, respectively. The angle polarizers 44a–c may be monitored and controlled by electronics and post processing unit 20 to produce multiple, discrete polarization angles for the light 22a–c of each wavelength. Thereafter, a second modulating mechanism 46 may be implemented to modulate the polarization vector for all wavelengths. In this way, the polarization techniques of light 22a–c reduce, eliminate and/or minimize the impact of the ambient optical noise.

Figure 3C:
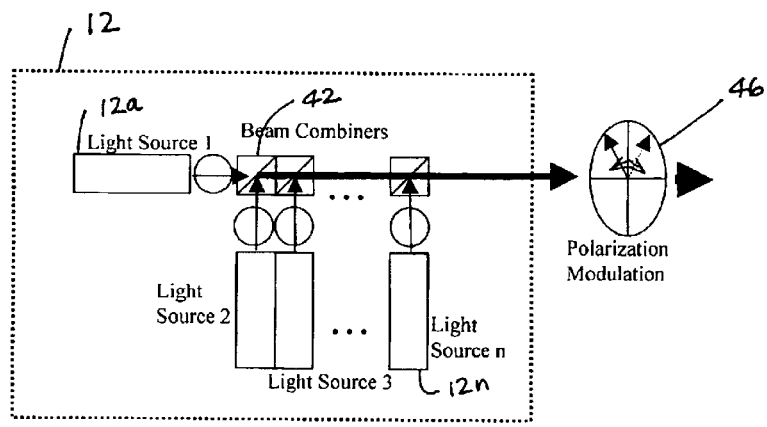

With reference to FIGS. 2D and 3C, in yet another embodiment, modulating mechanism 46 is employed at the output of the light source unit 12 without use of angle polarizers 44*a–i c*. In this embodiment, modulating mechanism 46 modulates the polarization vector for all wavelengths when multiple light sources 12*a–n* are used to produce light at multiple frequencies.

Figure 4A:
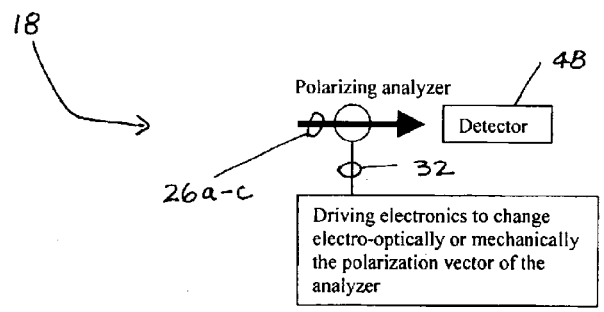
FIGS. 4A–4C illustrate embodiment of the detection system according to various aspects of the present invention, including a single detector receiving light at a fixed or discrete set of polarization angles (FIG. 4A), two detectors receiving light with orthogonal polarization vectors (FIG. 2B), and a plurality of detectors (i.e., more than two detectors) to receive light at any given set of discrete polarization angles (FIG. 4C)

As mentioned above, detector unit 18 measures the intensity of light output by polarizing analyzer optics 16. With reference to FIG. 4A, in one embodiment, detector unit 18 includes one or more detectors that receive light at a fixed or discrete set of polarization angles. For example, the detector (s) may be a silicon photodiode that can receive, measure, sense and sample light in the visible and near infrared spectrum.

Figure 4B:
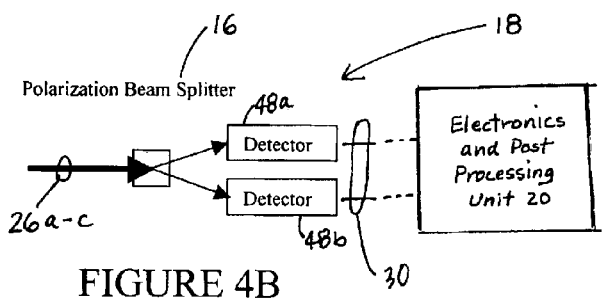

In another embodiment, system 10 includes at least two detectors. With reference FIG. 4B, light detectors 48*a* and 48*b* receive light with polarization vectors orthogonal to one another. In this regard, polarizing analyzer optics 16 includes a polarization beam splitter such as a Wollaston prism that "splits" the light beam into orthogonal linear polarizations. Thereafter, detectors 48*a* and 48*b* measure the intensity of the light and provide that information to electronics and post processing unit 20.

Figure 4C:
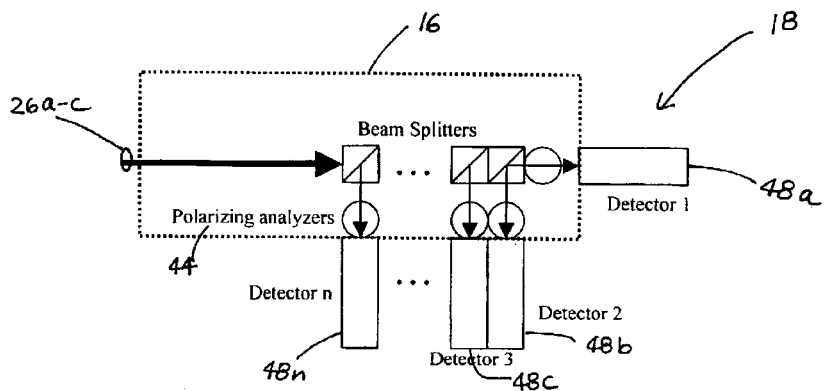

In yet another embodiment, system 10 includes more than two detectors. With reference to FIG. 4C, detectors 48*a–n*, via polarization optics 16, receive different polarization states for compensating for noise such as motion artifact and corneal birefringence. The polarization optics may include, for example, fixed or variable polarizers or waveplates to provide light at any given set of discrete polarization angles to detectors 48*a–n*.

Figure 5:
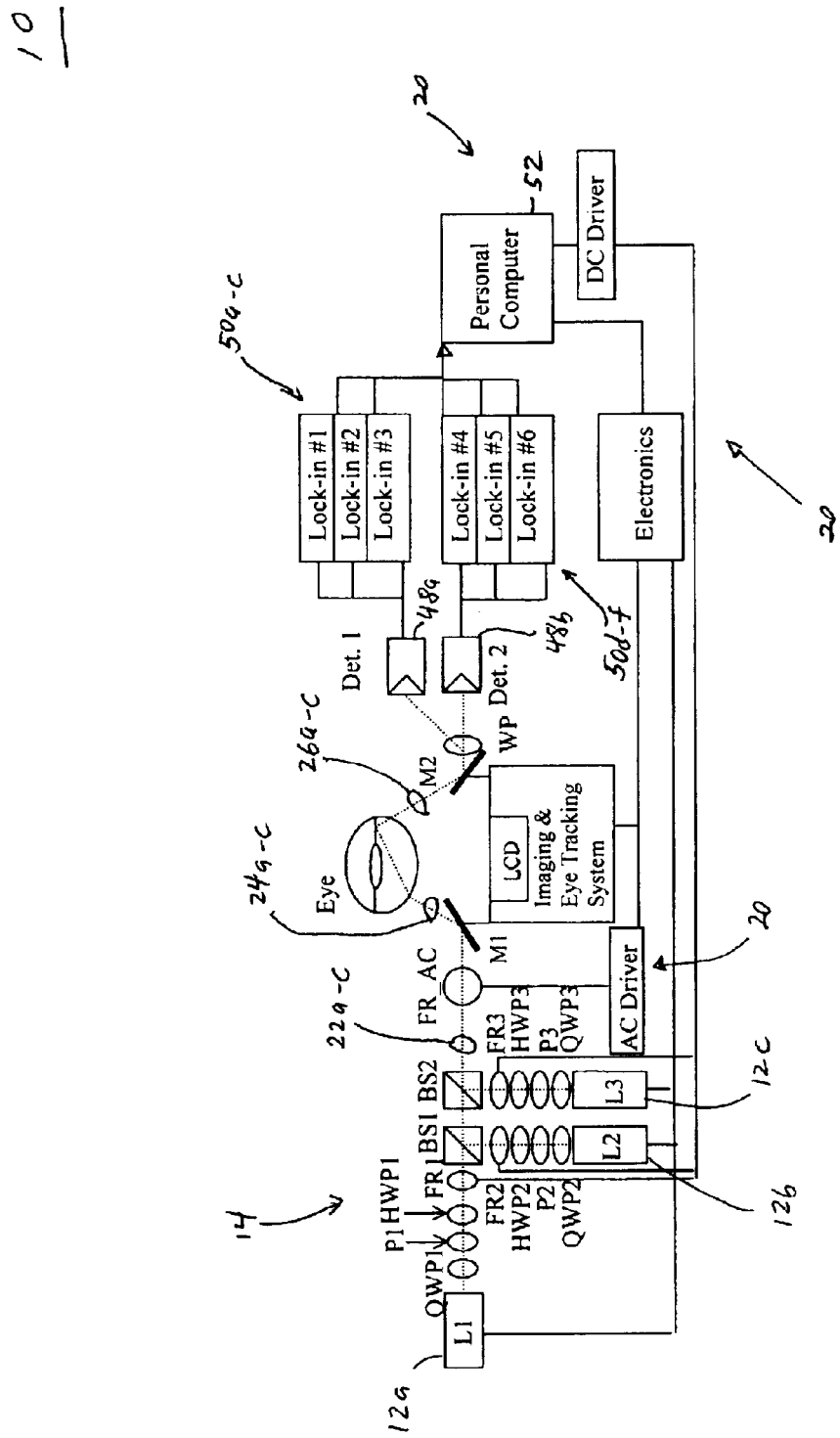
FIG. 5 illustrates an embodiment of the present invention including a three wavelength system that employs three laser light sources, three quarter waveplates for noise reduction, three half waveplates for discrete variation in the input polarization angle for each wavelength, electro-optical rotators for feedback to produce a closed-loop system and improve system stability, an ac-coupled electro-optical polarization modulator to produce the modulation of the polarization vector, a Wollaston prism to split the output polarization, a dual detector and synchronous modulation electronics, data processing system and an eye tracking imaging system.

With reference to FIG. 5, in one set of embodiments, system 10 includes three light sources 12*a–c* (for example, lasers) having dedicated optics and electronics, coupled thereto, to provide light 22*a–c* having a plurality of wavelengths. In one embodiment, light sources 12*a-c* provide light having a wavelength from about 450 nm to about 850 nm. Moreover, in one embodiment, light sources 12*a–c* are modulated at separate frequencies.

Figure 6:
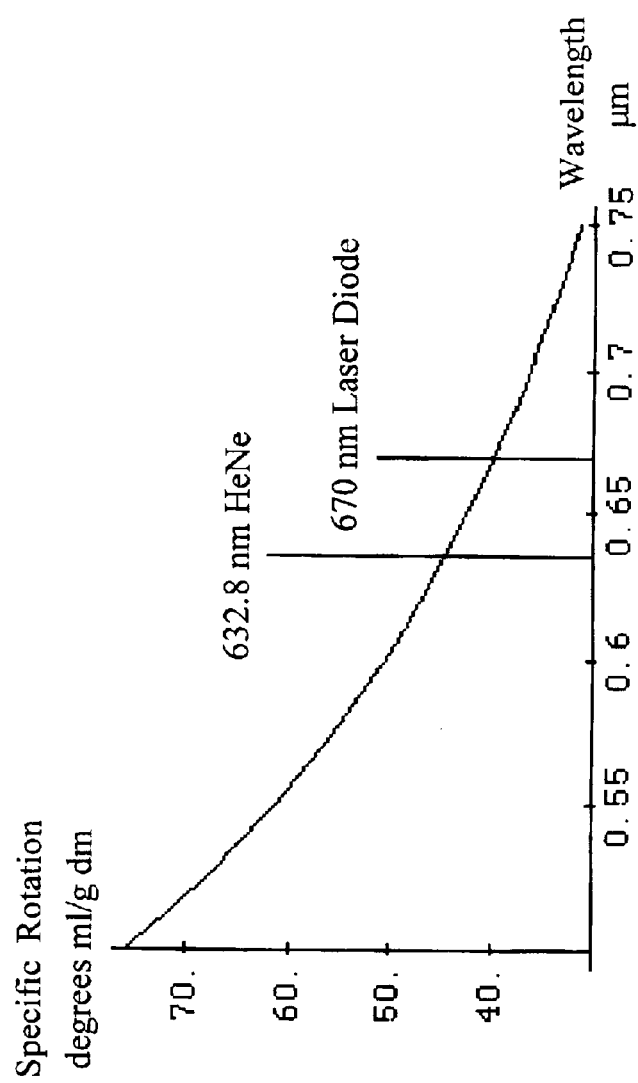
FIG. 6 illustrates an optical rotatory dispersion curve for glucose across the visible and near-infrared spectrum.

In particular, the wavelengths of each light source 12*a–c* may include the visible and near-infrared spectrum, so as not to cause damage from UV rays, and take advantage of the different rotations with wavelength shown in the optical rotatory dispersion curve for glucose (FIG. 6). For example, in those instances where light sources 12*a–c* are lasers, the laser wavelengths that are commercially available and cover the range are at or near 532 nm, 650 nm, and 830 nm. Moreover, each laser may be modulated at a separate frequency that would allow their synchronous separation and detection by detectors 48*a* and 48*b*. The modulation frequency may be in the kilohertz range to avoid the noise due to the 60 hertz room lights and facilitate implementation of conventional electronic synchronous detection.

The dedicated optics and electronics includes, for example, quarter waveplates QWP1–QWP3, optically located at the output of light sources 12*a–c*, to reduce laser polarization noise that may be produced by sources 12*a–c*. In this regard, quarter waveplates QWP1–QWP3 may be aligned with the preferred laser polarization axis to minimize the polarization noise of sources 12*a–c*. The quarter waveplates QWP1–QWP3 may be manufactured with spatial variability or may be electro-optically controlled to vary at discrete, predetermined points in time.

In addition, the dedicated optics and electronics also includes polarizers P1–P3 that linearly polarizes the beam at ±45° relative to the quarter-wave plate, and half waveplates HWP1–HWP3, optically located at the output of polarizers P1–P3. The half waveplates HWP1–HWP3 permit linear polarization at any angle. In this way, the beam is aligned with the fast or slow axis of birefringence of the cornea. Thus, each light beam 22*a–c* may be linearly or circularly polarized at any angle. Notably, half waveplates HWP1–HWP3 may be spatially variable or electro-optically controlled and/or monitored by, for example, electronics and post processing unit 20.

The system 10 may also include a set of polarization rotators FR1–FR3 (for example, faraday rotators) to facilitate feedback of an output voltage that is proportional to the fundamental harmonic and to the glucose concentration. In this way, system 10 may "null" each optical path of the light 22*a–c* for enhanced sensitivity and stability.

Two beam combiners BS1 and BS2 combine the three beams along one path. Thereafter, in one embodiment, light beams 22*a–c* are directed through a polarization rotator FR_AC (for example, faraday rotator or an electro-optic polarization rotator including birefringent crystals and pockel cells) that modulates the polarization vector of the light beam. In one embodiment, polarization rotator FR_AC provides an output voltage (via feedback) that is proportional to the fundamental harmonic of the light beam.

The light 24*a–c* may be directed onto the eye using a mirror or an electro-optic device M1. The combined light 24*a–c* is directed through the anterior chamber of the eye. In one embodiment, electro-optic device M1 is a piezo-electric mirror that is controlled by an image tracking system. The image tracking system tracks motion of the eye and controls the electro-optic device to maintain appropriate, desired or correct alignment of beam 24*a–c* relative to or in the presence of eye motion and/or movement. Indeed, in one embodiment, a second electro-optic device M2 works in combination with the image tracking system to maintain appropriate, desired and/or correct alignment of beam 26*a–c* relative to or in the presence of eye motion or movement.

The image tracking system tracks eye motion to maintain the light beam in the proper, suitable and/or desired orientation through the anterior chamber of the eye in the presence of eye motion, which may include reflection of the light beam off of the iris or lens of the eye. Moreover, the present invention may also include a visible stimulus (for example, an LCD or CRT display) to encourage the patient to maintain the eye focused and steady during operation of system 10. A visible stimulus may more easily permit the patient to fixate the eye and thereby remove gross motion artifacts.

The second electro-optic device M2 directs the modified light 26*a–c* onto a polarization beam splitter WP (such as a Wollaston prism). The beam splitter WP splits light 26*a–c* into orthogonal linear polarizations.

Thereafter, at least two light detectors 48*a* and 48*b* receive each orthogonal beam and generate a current carries direct current, first harmonic, and second harmonic information for each wavelength that can be used to determine the rotations due to the glucose concentration in the eye (and eliminate or minimize issues pertaining to ambient noise).

In one embodiment, at least six synchronous demodulators (for example, lock-in amplifiers) 50*a–f*, three demodulators for each detector, provide information regarding the fundamental and second harmonic signals for each orthogonal polarization at each wavelength. The output of each demodulator is provided to a computing system 52 (which is a part of electronics and post processing unit 20). The computing system 52 may be used to acquire the signals digitally and is coupled to electronics to calculate and store the glucose concentration as well as provide feedback to each of the four polarization modulations, three light sources, and imaging/eye tracking system. An LCD or CRT may be used to display the output concentration and force the patient to focus the eye.

In operation, system 10 senses an analyte in the aqueous humor of the eye using a combination of wavelengths from simultaneous or sequentially fast (microseconds or less) light beams, each having different optical wavelengths and different modulation frequencies from one another. According to one embodiment, the change in polarization of the light beams is detected by decomposing the light beams into orthogonal linear polarizations, detecting each orthogonal beam with a photodetector that generates a photocurrent that carries direct current, first harmonic and second harmonic information for each wavelength, demodulating the photocurrent for each of the orthogonal polarizations to provide the fundamental and second harmonic signal for each orthogonal polarization, computing the change in the polarizations and relating the change to glucose concentration. According to one embodiment a display displays the computed glucose concentration.

EXAMPLES

The following examples are included to provide, among other things, background information to demonstrate, for example, advantages of the present invention. The techniques, systems and devices described and illustrated in the EXAMPLES that follow, in some sense, may be preferred modes of practice. This notwithstanding, it is understood that various combinations of the structures, components, materials, techniques and/or elements, other than those specifically shown and described herein, are contemplated and/or recognized by those skilled in the art. Accordingly, such various combinations of the structures, components, materials, techniques and/or elements are within the scope of the present invention.

Moreover, while certain embodiments, features, materials, configurations, attributes and advantages of the inventions are described below in the EXAMPLES, it should be understood that many other, as well as different and/or similar embodiments, features, materials, configurations, attributes, structures and advantages of the present inventions that are apparent from the descriptions and illustrations pertaining to the EXAMPLES. As such, the embodiments, features, materials, configurations, attributes, structures and advantages of the inventions described and illustrated herein are not exhaustive and it should be understood that such other, similar, as well as different, embodiments, features, materials, configurations, attributes, structures and advantages of the present inventions are within the scope of the present invention.

Materials and Methods
Optical Rotatory Dispersion of Analytes in the Eye

Briefly, by way of background, in order to understand optical rotatory dispersion (ORD), one must first understand that the polarimetric approach is based on the fact that chiral molecules, such as glucose, due to their asymmetric nature, rotate the azimuthal angle of the polarization vector of a propagating linear polarized beam. This rotation, $\alpha$, is proportional to the analyte concentration, C, for a given pathlength, L, pH, temperature, T, and wavelength, $\lambda$. An equation for this effect may be expressed as:

$$[\alpha]_{\lambda, pH}^{T} = \frac{\alpha}{LC} \tag{1}$$

where $[\alpha]_{\lambda, pH}^{T}$ is a unique rotation of the particular molecule.

For a given chiral substance, the wavelength dependence of specific rotation provides the Optical Rotatory Dispersion (ORD) characteristics of the constituent molecule. This is expressed in EQUATION 2, which is an approximation of Drude's equation and may be useful between the absorption bands for a given molecule.

$$[\alpha]_{\lambda, pH}^{T} = \frac{k_o}{\lambda^2 - \lambda_o^2} \tag{2}$$

With reference to EQUATION 2, once the constants $k_o$ and $\lambda_o$ are computed or determined by evaluating or considering the specific rotation at (at least) two different wavelengths, the specific rotation for any wavelength, $\lambda$, within the range, may be determined where the pH and temperature are fixed or relatively constant.

In those situations where more than one chiral component is present within a sample or fluid, determining the specific rotation at different wavelengths may enable the isolation of the contributions of a particular analyte, including an analyte of interest. This may be accomplished by applying the superposition theorem to build a multispectral regression model. Notably, knowing the ORD characteristics for each constituent chiral component enables the optimal selection of wavelengths to produce the best possible prediction model, for the analyte of interest.

Corneal Birefringence

Birefringence may be described as the condition in which two orthogonally oriented differing refractive indices of light exist for a substance due to its physical and/or molecular structure. These are described as the ordinary refractive index, $\eta_o$ (along the slow axis), and the extra-ordinary refractive index $\eta_e$ (along the fast axis). The cornea of the eye is known to be a birefringent material.

In the experiments described herein, the eye was modeled as a "linear retarder". This means that for a linear input polarization state, the eye's linear birefringence effects a change in the state of polarization (SOP) from a linear to an elliptical state, due to the introduced phase retardance, $\delta$, as defined in EQUATION 3. As such, a change in the detected signal, as the ellipticity of the ensuing elliptically polarized beam, varies with the changes in birefringence ($\eta_o - \eta_e$).

$$\delta = \frac{2\pi t}{\lambda}(\eta_o - \eta_e) \tag{3}$$

Were the cornea to be a stable, fixed, birefringent element such as a waveplate, its effects may be theoretically eliminated. However, corneal birefringence may become problematic when there is motion artifact because the effect of non-stationary birefringence may mask the glucose signature. To assess the significance of birefringence, a spectral analysis of in vivo data from a rabbit was obtained and analyzed.

In order to "compensate" for motion induced corneal birefringence artifacts, it may be advantageous to have a better understanding of how birefringence changes affect the detected measurement signal. This was approached from a simulation and experimentation perspective. Both the simulation and experimental results are described separately below.

Results and Discussion

Figure 7:
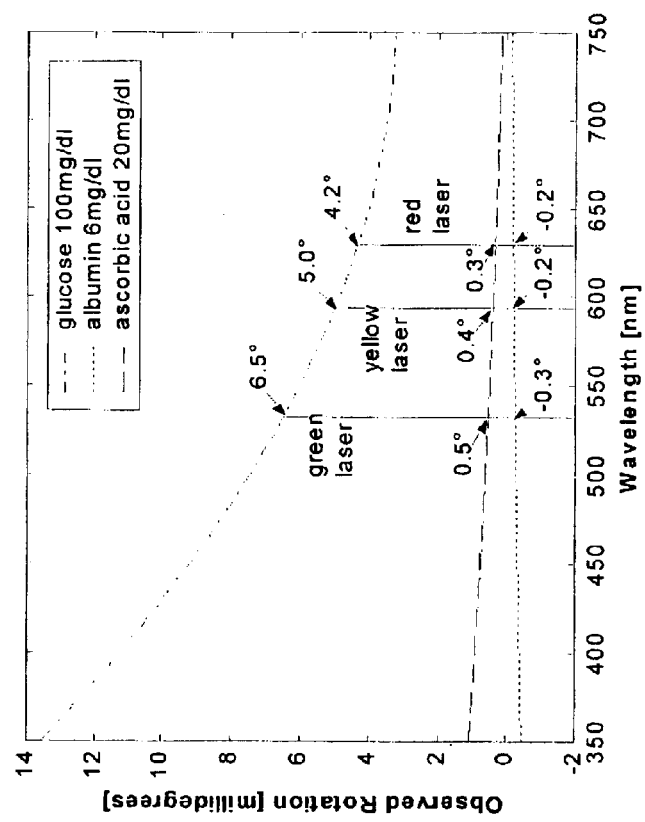
FIG. 7 illustrates observed or measured optical rotations for physiological concentrations of aqueous humor analytes, glucose, albumin, and ascorbic acid for a 1 centimeter path length.

FIG. 7 illustrates the ORD curves ($\lambda$ from 350 nm to 750 nm), at a given pH and temperature, for glucose and two potential confounders, albumin and ascorbic acid. As evaluated at their average physiological levels, they are relatively negligible, particularly at higher wavelengths. This is based on the assumption that any fluctuations in their concentrations within their full physiological ranges will be minimal and slow in the aqueous humor compared to those of glucose. In addition, these two components are contra-rotatory and thus may (partially) cancel each other. Therefore, it is unlikely that these optically active substances in the eye will significantly affect the glucose signal. However, if necessary, a multi-wavelength system should enable the compensation of any confounding effects due to other chiral analytes.

Corneal Birefringence Results

Characterization of Corneal Motion Artifact

Figure 8:
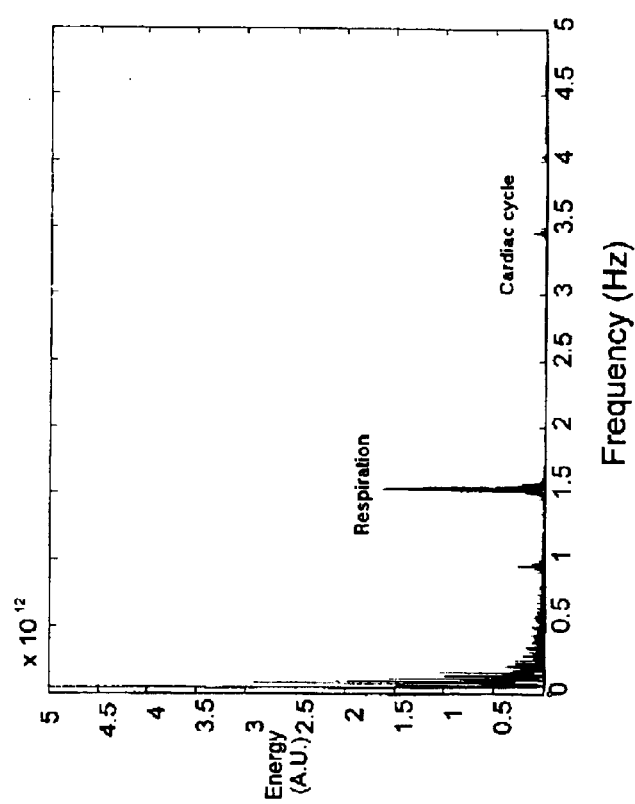
FIG. 8 illustrates a fast Fourier Transform (FFT) of the detected signal from an in vivo study aimed at measuring glucose optical rotation in an anesthetized rabbit.

FIG. 8 illustrates the motion induced corneal birefringence artifact for the in vivo rabbit experiment. In short, this experiment reveals that such an artifact was found to be primarily due to respiratory motion and, to a limited extent, the cardiac cycle. Since the motion induced corneal birefringence artifact may be attributed to the respiration and the cardiac cycle and not to random eye motion, it may be difficult to remove or eliminate the artifact (for instance, where the patient is a human, by asking the person to cease eye motion by, for example, focusing their vision on a given object). Thus, it may be advantageous to further or better understand the corneal birefringence across the eye and develop of a method for measurement in the presence of moving corneal birefringence.

Corneal Birefringence Simulation Results

Figures 9A, 9B:
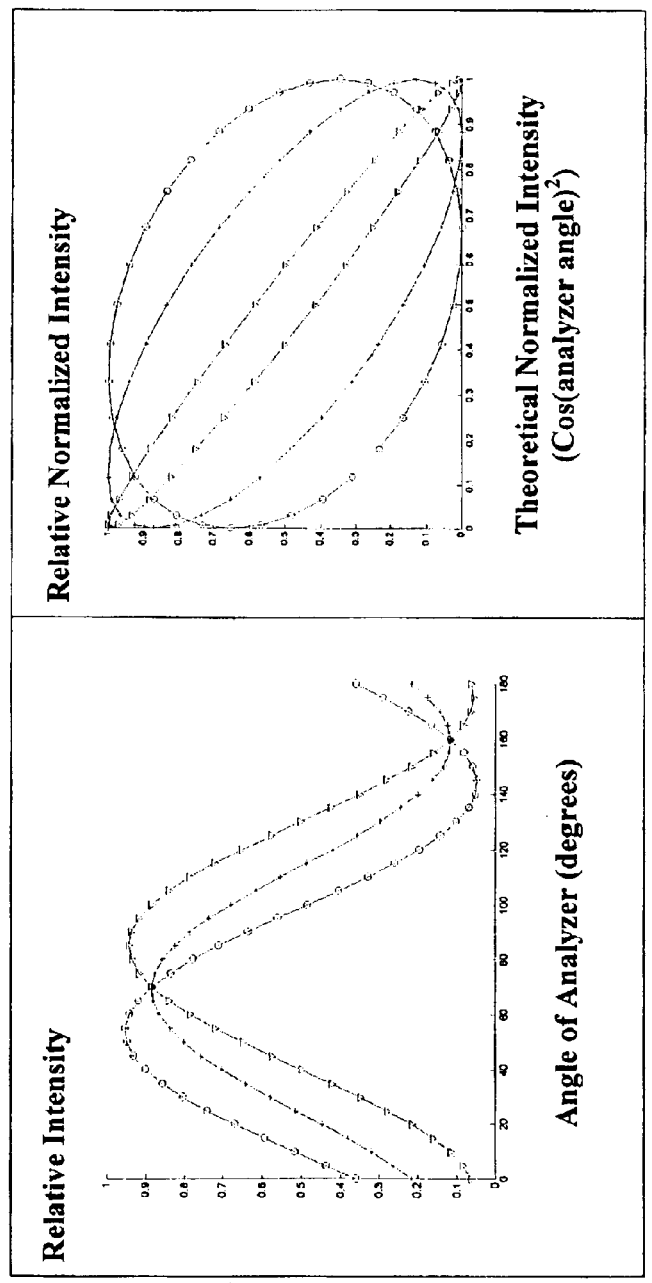
FIGS. 9A and 9B illustrate MATLAB derived simulations of the effects of changing birefringence, ($\eta$o–$\eta$e), on the detected intensities (the index difference varied from $1\times10^{-4}$ (triangle), $2\times10^{-4}$ (diamond), $3\times10^{-4}$ (circle))

FIGS. 9A and 9B are MATLAB generated simulations of the effects of linear birefringence. The birefringence values used for the simulation are within the range based on the measured refractive index variations available in literature for the fast and slow axes of rabbit cornea. Briefly, ($\eta_o - \eta_e$) varies in the eye within the range of zero at the apex or top of the cornea to $5.5 \times 10^{-04}$ at the base of the cornea, where it attaches to the sclera. Therefore, a net change in the retardance, $\delta$, may be calculated using EQUATION 4 for a given corneal thickness, t and wavelength, $\lambda$.

In short, the graphical representations illustrated in FIGS. 9A and 9B were derived by modeling the rotation of the analyzer with respect to the polarizer to determine the effect of a birefringent sample placed in between them. For a birefringent crystal the detected intensities vary sinusoidally as the polarizer/analyzer plane is rotated through 180°. The birefringence has the effect of introducing a phase shift in the detected intensities (FIG. 9A).

FIG. 9B was produced by plotting the modeled detected intensity at a given angle verses the normalized theoretical detection intensity for a polarizer and rotating analyzer combination without a sample, (i.e. the cosine squared of the input angle). Without birefringence, a straight line would be expected. With a changing birefringence, the conversion of the linear polarization into elliptical polarization states of varying ellipticity and azimuthal angle of the major axis is observed.

The results set forth in FIGS. 9A and 9B may substantiate the changes of a horizontal linear SOP into an elliptical SOP whose ellipticity changes with variations in the sample birefringence when the input SOP is neither aligned with the slow or fast axis of birefringence. For this simulation a fast axis of birefringence of 160 degrees was used, comparable to that found experimentally, and the value of the retardance was varied by varying the refractive indices around the center of the eye ($1.0 \times 10^{-04}$ to $3.0 \times 10^{-04}$) for a given corneal pathlength of 0.407 mm and wavelength of 633 nm. This variation showed a slight shift in the minimum as seen in FIG. 9A and spreading of the ellipse as depicted in FIG. 9B. This may be comparable to slight changes in the retardance with position of the beam on the cornea as is likely the case for the three eyes used in the experiment.

Experimental Corneal Birefringence Results

Figures 10A, 10B:
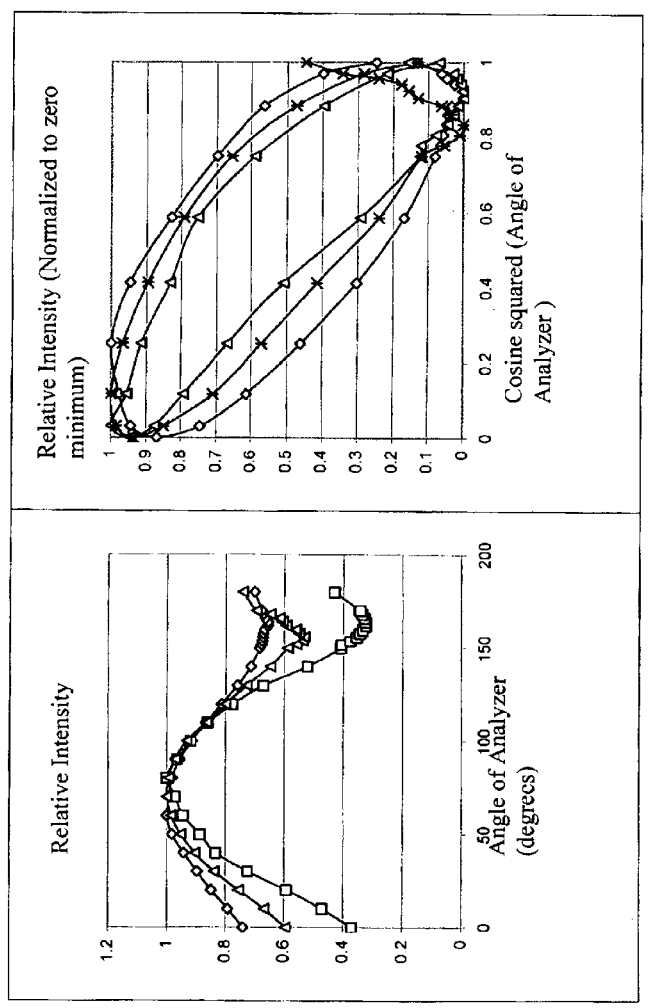
FIG. 10A illustrates a normalized graphical representation of corneal birefringence from three different rabbit eyes showing a minimum and hence fast axis of birefringence at approximately 160 degrees.
FIG. 10B illustrates a graphical representation of the cosine of the angle of the analyzer squared (from 0 to 180 degrees) versus the normalized values in which the minimum for each plot was set to zero; this shows the characteristic elliptical birefringence.
Figure 11:
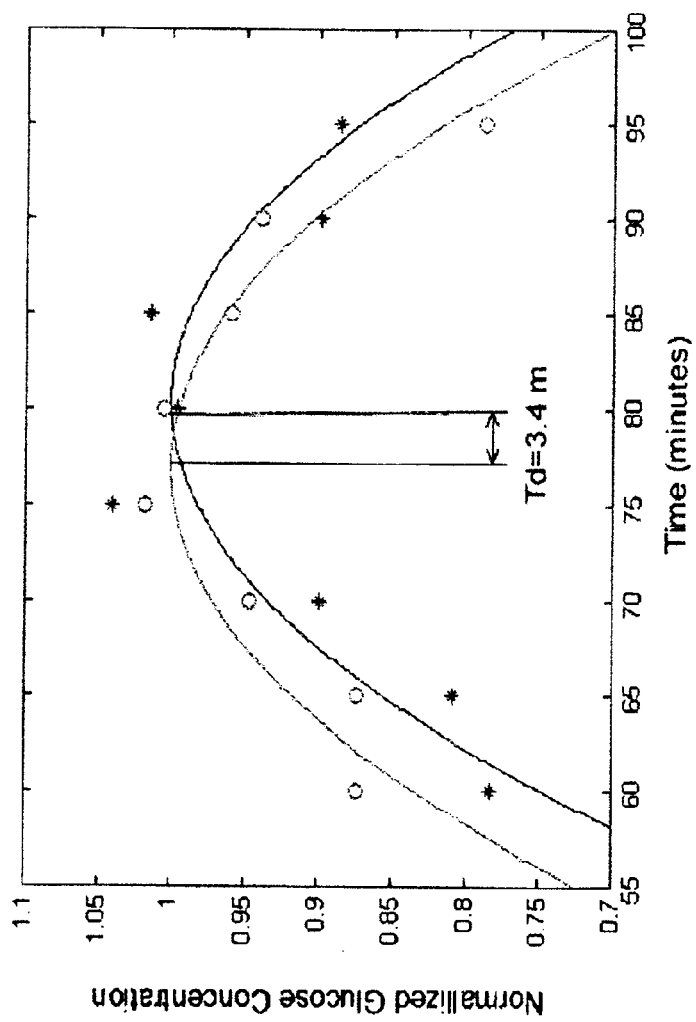
FIG. 11 illustrates the measured glucose transport time delay between the blood and aqueous humor in a rabbit.

With reference to FIG. 10A, the birefringence curves for three separate rabbit eyes reveals that the minimum point varies slightly between eyes. The light beam was centered at roughly the midpoint between the apex of the cornea and the base of the cornea (where it meets the sclera). The minimum point that varies slightly between eyes may be due to a slight change in the retardance between eyes as a result of a slightly different index of refraction change.

In addition, this change in birefringence is illustrated in FIG. 10B by the change in ellipticity. Notably, the simulations illustrated in FIG. 9B (in which the retardance has been varied) confirm the results illustrated in FIG. 10B. The change in corneal retardance is likely due to the well-documented change in corneal retardance with position from the apex of the cornea. This confirms that slight changes in position with motion artifact can greatly affect the polarization signal. These recent findings are encouraging and suggest that the birefringent portions of the corneal surface, in a rabbit model, all have a relatively universal fast axis located at approximately 160° from the vertical axis, defined as a line that runs from the apex of the cornea and through the pupil. Though more rabbit eyes need to be investigated with the light source at various locations across the cornea, this preliminary finding coupled with the understanding of how birefringence affects the detected signal, allows for the theoretical elimination of the effects of changing birefringence on the measurement of the azimuthal rotation of the linear polarization vector due to glucose.

The use of polarized light in the aqueous humor of the eye has been described as a technique of non-invasively quantifying blood glucose levels. For normal physiologic ranges of analytes other than glucose in the aqueous humor and for the wavelength range above 350 nm, their contributions may be negligible. However, the prediction errors for glucose may be improved if a multi-wavelength system and techniques are employed to compensate for the impact of these other analytes.

Finally, the effect of changing corneal birefringence on glucose measurements has been characterized in vivo and the system modeled and characterized for the eye in vitro. This information enables the design and implementation of a closed loop multi-wavelength, multi-frequency, and multi-polarization system that facilitates the accurate and repeatable measurement of glucose in vivo.

There are many inventions described and illustrated herein. While certain embodiments, features, materials, configurations, attributes and advantages of the inventions have been described and illustrated, it should be understood that many other, as well as different and/or similar embodiments, features, materials, configurations, attributes, structures and advantages of the present inventions that are apparent from the description, illustration and claims. As such, the embodiments, features, materials, configurations, attributes, structures and advantages of the inventions described and illustrated herein are not exhaustive and it should be understood that such other, similar, as well as different, embodiments, features, materials, configurations, attributes, structures and advantages of the present inventions are within the scope of the present invention.

What is claimed is:

1. A system for sensing an analyte in the aqueous humor of the eye of a patient, the system comprising:

a light source unit to provide at least three light beams wherein each light beam includes a wavelength and modulation frequency that is different from the other light beams;

a polarization mechanism, optically positioned to receive the light beams, and to linearly polarize each light beam;

a detector unit, optically positioned to receive the light beams reflected by the eye, to detect a change in polarization of the light beams, wherein the polarization of the light beams are changed as a result of contact with analyte in the aqueous humor of the eye; and a processing unit, coupled to the detector unit, to determine the concentration of analyte in the aqueous humor of the eye using information which is representative of the change in polarization of the light beams.

2. The system of claim 1 wherein the light source unit includes a plurality of lasers.

3. The system of claim 1 wherein each light beam is linearly polarized at any angle.

4. The system of claim 1 wherein the polarization mechanism is a polarization rotator.

5. The system of claim 4 wherein the polarization rotator feeds back an output voltage proportional to the fundamental harmonic of the light beam.

6. The system of claim 5 wherein the polarization rotator is a faraday rotator.

7. The system of claim 1 wherein the polarization mechanism modulates the polarization vector of at least two of the light beams.

8. The system of claim 7 wherein the polarization rotator is a faraday rotator.

9. The system of claim 1 further including a beam steering mechanism to direct the beams through the anterior chamber of the eye of the patient.

10. The system of claim 9 wherein the beam steering mechanism is an electro-optic device.

11. The system of claim 10 wherein the electro-optic device is a piezo-electric mirror.

12. A system for sensing an analyte in the aqueous humor of the eye of a patient, the system comprising:

a light source unit to provide at least three light beams wherein each light beam includes a wavelength and modulation frequency that is different from the other light beams;

a polarization mechanism, optically positioned to receive the light beams, and to linearly polarize each light beam;

a beam steering mechanism, optically positioned to receive linearly polarized light beams, that is capable of directing the linearly polarized light beams through the anterior chamber of the eye of the patient;

an image tracking unit, coupled to the beam steering mechanism, to control the beam steering mechanism in response to motion of the eye of the patient;

a detector unit, optically positioned to receive the light beams reflected by the eye, to detect a change in polarization of the light beams, wherein the polarization of the light beams are changed as a result of contact with analyte in the aqueous humor of the eye; and a processing unit, coupled to the detector unit, to determine the concentration of analyte in the aqueous humor of the eye using information which is representative of the change in polarization of the light beams.

13. The system of claim 12 wherein the light source unit includes a plurality of lasers.

14. The system of claim 12 wherein each light beam is linearly polarized at any angle.

15. The system of claim 12 wherein the polarization mechanism is a polarization rotator.

16. The system of claim 15 wherein the polarization rotator feeds back an output voltage proportional to the fundamental harmonic of the light beam.

17. The system of claim 16 wherein the polarization rotator is a faraday rotator.

18. The system of claim 12 wherein the polarization mechanism modulates the polarization vector of at least two of the light beams.

19. The system of claim 12 wherein the beam steering mechanism is an electro-optic device.

20. The system of claim 19 wherein the electro-optic device is a piezo-electric mirror.

* * * * *